United States Patent [19]

Peters

[11] 4,191,543
[45] Mar. 4, 1980

[54] STERILE AIR RECYCLING APPARATUS

[76] Inventor: Max D. Peters, 633 Turnpike Rd., Minneapolis, Minn. 55416

[21] Appl. No.: 863,911

[22] Filed: Dec. 23, 1977

[51] Int. Cl.² .................. B01D 46/42; B01D 46/54
[52] U.S. Cl. ........................... 55/279; 55/338; 55/385 A; 55/414; 55/419; 55/473; 55/DIG. 18; 55/DIG. 29; 98/40 D; 422/122
[58] Field of Search .............. 55/338, 385 A, 414, 55/419, 473, DIG. 18, DIG. 29, 279; 98/40 D; 21/74 R

[56] References Cited

U.S. PATENT DOCUMENTS

| | | | |
|---|---|---|---|
| 2,135,461 | 11/1938 | Woolley | 55/DIG. 29 |
| 3,395,972 | 8/1968 | Hardison | 55/DIG. 18 |
| 3,669,349 | 6/1972 | Hall, Jr. | 98/40 D |
| 3,721,067 | 3/1973 | Agnew | 55/385 A |
| 3,828,530 | 8/1974 | Peters | 55/473 |
| 3,960,527 | 6/1976 | Goettl | 55/419 |
| 4,034,659 | 7/1977 | Raider | 55/DIG. 29 |
| 4,061,082 | 12/1977 | Shuler | 55/DIG. 29 |
| 4,094,232 | 6/1978 | Howorth | 55/DIG. 29 |

FOREIGN PATENT DOCUMENTS 1362249 7/1974 United Kingdom ............ 55/473

OTHER PUBLICATIONS

Federal Standard Clean Room and Work Station Requirements, Controlled Environment, Nuaire, Inc.

Primary Examiner—David L. Lacey
Attorney, Agent, or Firm—Clayton R. Johnson

[57] ABSTRACT

A sterile air recycling module is mounted to a wall of a room and includes a housing having an outlet for discharging sterile or clean air into the room, opposed grilled inlets for controlling the volume of air drawn into the interior of the housing from the room, and an inlet for fresh air or plant conditioned air, a supply pressure plenum chamber within the housing for discharging air through a high efficiency particulate air (HEPA) filter which is in fluid communication with the housing outlet, and a blower within the housing for withdrawing air from a negative pressure plenum within the housing and an outlet in fluid communication with the supply pressure plenum, the housing inlets being in fluid communication with the negative pressure plenum.

7 Claims, 4 Drawing Figures

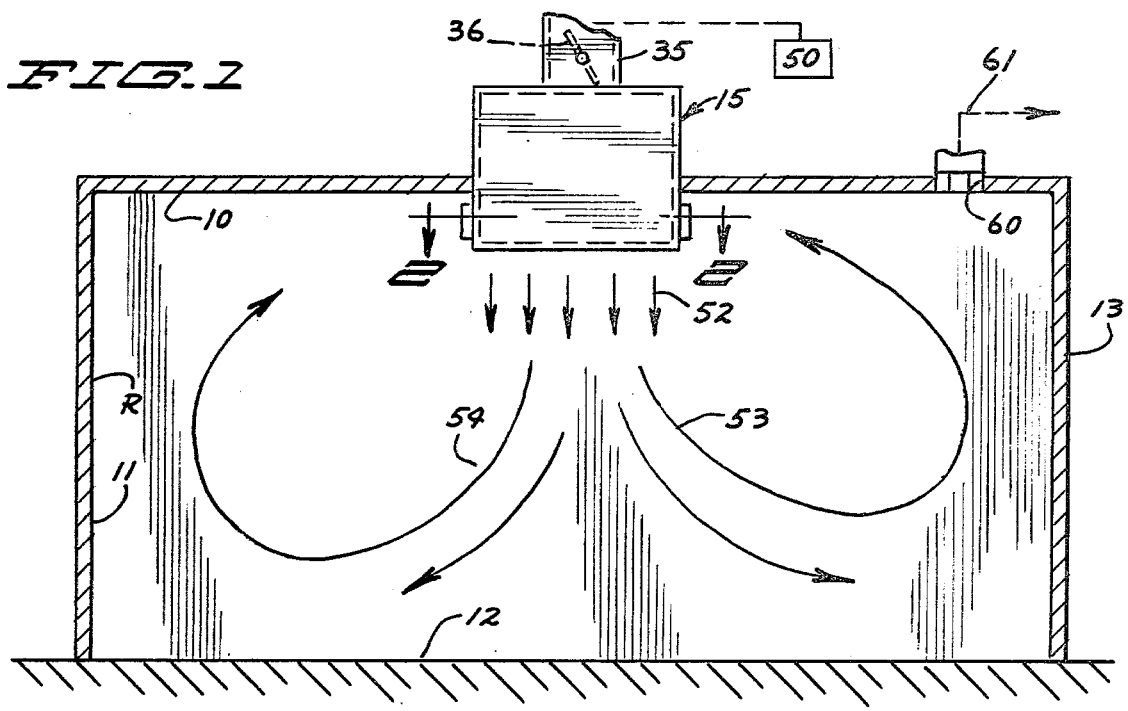
FIG. 1
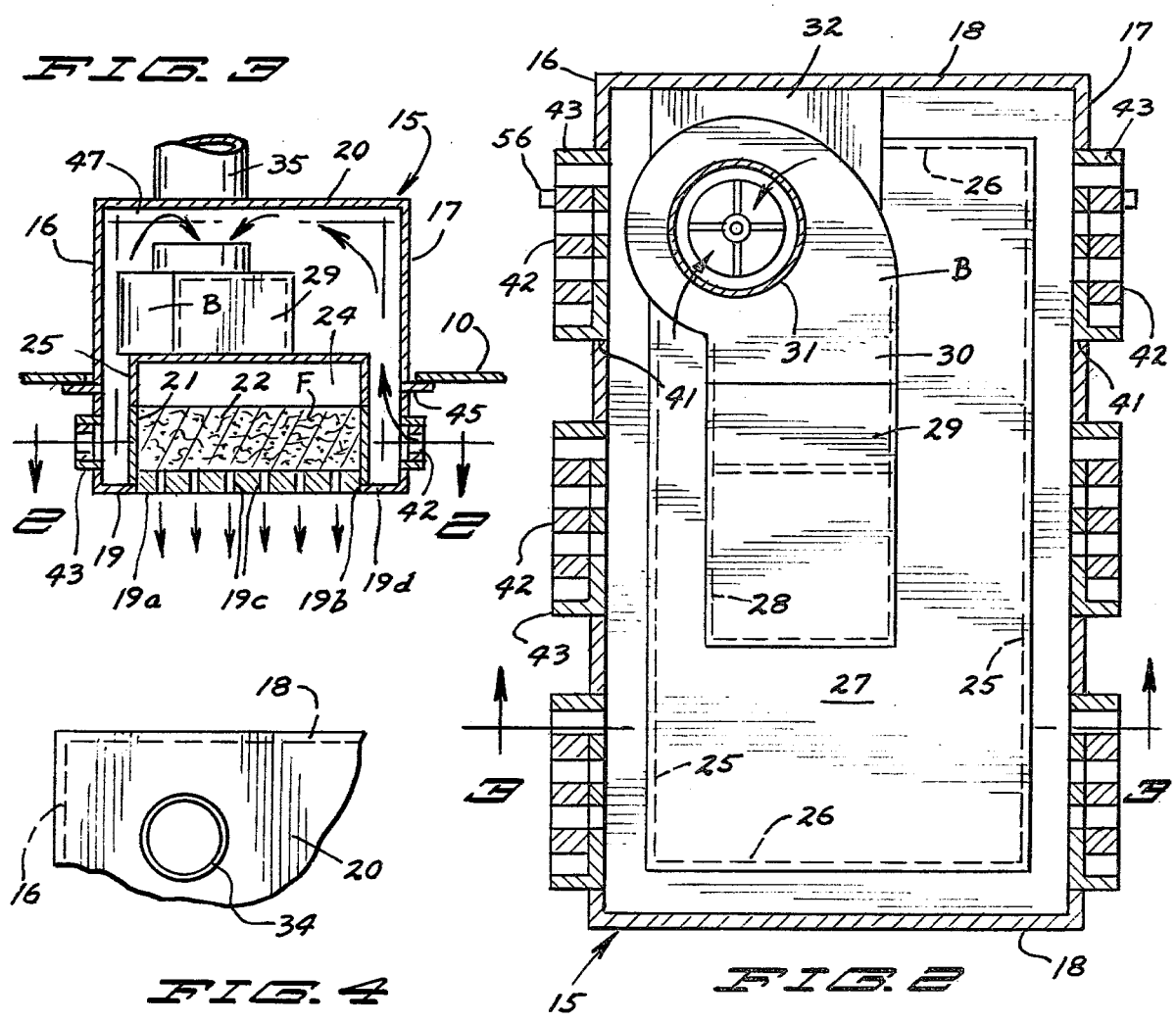
FIG. 3
FIG. 4
FIG. 2

STERILE AIR RECYCLING APPARATUS

BACKGROUND OF THE INVENTION

A sterile air module that includes a high efficiency particulate air filter and a blower for discharging air under pressure through the filter.

In the prior art it is old to provide a filter system for a clean room that includes a housing having a single air inlet, and an outlet, a high efficiency particulate air filter in the outlet, and a blower in the housing for drawing air in through the inlet and discharging air through the filter to pass through the outlet; for example see my U.S. Pat. No. 3,828,530. Further it is old to provide clean rooms, free from particulate matter and suitable for medical research, surgery theaters, patient care rooms, and sophisticated industrial processes by circulating HEPA filtered air downwardly from ceiling to floor or across from wall to wall, in each case carrying return room air through ducts external to the room back to blowers and HEPA filters for recycling. However, such prior art filter systems do not provide for both recirculating room air and discharging fresh air into the room. In order to provide a sterile air module that filters both recycled room air and fresh air, this invention has been made.

SUMMARY OF THE INVENTION

A sterile air room module for a clean room that has a fresh air inlet, room air inlets, a filtered air outlet, a high efficiency particulate air filter in the outlet and a blower for drawing air through the inlets and discharging air to pass through the filter and the outlet.

An object of this invention is to provide new and novel means for recycling room air and fresh air and filter the air before discharge into the room to result in an air quality that meets Federal Standard 209b. Another object of this invention is to provide new and novel means for selectively controlling the amount of fresh makeup air discharged into a room and independently selectively controlling the rate of recycling air in the room with both the fresh air and recycled air being HEPA filtered before being discharged into the room.

BRIEF DESCRIPTION OF THE DRAWINGS

FIG. 1 is a somewhat schematic showing of the apparatus of this invention mounted in a room for recycling room air and discharging fresh air into the room;

FIG. 2 is a horizontal cross sectional view of the sterile air recycling module of this invention, said view being generally taken along the line and in the direction of the arrows 2—2 of FIG. 3;

FIG. 3 is a transverse vertical cross sectional view generally taken along the line and in the direction of arrows 3—3 of FIG. 2; and FIG. 4 is a fragmentary view of the wall of the module that has the fresh air opening therein.

Referring now to the drawings, there is schematically shown a room having a ceiling 10, a floor 12 and side walls 11 and 13. The sterile air recycling module of this invention, generally designated 15, is mounted to the ceiling to extend therethrough, the module including opposite side walls 16 and 17, opposite end walls 18, a front or bottom wall 19, and a top or rear wall 20. The bottom wall 19 includes a perimetric flange portion 19d that defines an opening 19b in which an air diffuser panel 19a is mounted. The panel 19a has a plurality of air diffuser passageways 19c extending therethrough for discharging air vertically downwardly into the room interior.

Mounted in the housing interior is a high efficiency particulate air (HEPA) filter F that includes a filter frame 21 and filter material 22. The filter F has at least a 75 percent efficiency for the removal of 0.3 micron particles as determined by the standard D.O.P. Test of the Army Chemical Corps and preferably provides 99.9 percent removal of all aerosol particulate contaminants 0.3 microns or larger, as defined by government specifications TID-7023, High Efficiency Particulate Air Filter Units.

Plenum chamber side walls 25, end walls 26, and top wall 27 are joined together to in conjunction with the filter F define an air tight supply pressure plenum chamber 24 in fluid communication with the filter material 22. The plenum chamber top wall 27 is provided with an inlet opening 28, a flexible duct 29 being connected to the plenum chamber top wall for placing the inlet opening 28 in fluid communication with the outlet 30 of the blower B. The blower is mounted within the housing by a suitable blower mount 32 which may be mounted to one of end walls 18. The blower has an inlet 31 that opens within the housing and preferably is of an adjustable speed type for selectively varying the volume of air discharged thereby per unit of time.

The filter F, the supply pressure plenum 25–27, the duct 29, and the blower B are connected to one another and mounted in the housing to in conjunction with the housing walls defining a negative pressure plenum chamber 47 to which the blower inlet 31 opens. Thus, when the blower is operating, air in the negative pressure plenum chamber 47 is drawn through the inlet 31 to flow through the duct 29 and the supply pressure plenum chamber 24 to the filter F and then therethrough to be discharged through the diffuser panel openings 19c. Accordingly, when the blower is operating, the air that is discharged through the diffuser panel openings (both room air and fresh air) first flows through the filter to be filtered thereby.

For supplying fresh air to the negative pressure plenum 47, the housing top wall 20 is provided with an inlet opening 34, a duct 35 that provides fresh air to the inlet 34 being connected to a suitable conditioned air source 50, for example, rough filtered, heated or cooled, humidified or dehumidified air system that is usually installed in a building or plant for air ventilation purposes and usually provides air under pressure. The air flow from source 50 to the negative pressure plenum chamber 47 is controlled by a suitable valving component, for example a damper 36 mounted in the duct 35 (or may be a damper, not shown, mounted to wall 20 for partially or completely closing opening 34).

Each of the side walls 16 and 17 is provided with a plurality of grill inlet openings 41 that open to the room interior. Mounted within each grill opening is a grill frame 43 on which there is provided a movable grill 42 for adjustably controlling the volume of air flow through the grill opening. The grill members 42, 43 may be of any suitable conventional construction. For example each grill 42 may be provided with a knob 56 for moving grill 42 between a position to partially close the opening defined by grill frame 43 and a closed position to prevent air inflow through the respective opening 41. The grill openings open to the negative pressure plenum 47 and are located more remote from the housing top wall 20 than the flanges 45 that are joined to the walls 16-18 for mounting the module to the ceiling.

A suitable door (not shown) may be provided in one of the housing walls 16,17,18,20 or the diffuser panel mounted in a manner to permit changing the filter F and doing maintenance work on the blower.

A conventional room outflow grill 60, preferably adjustable, is provided in one of the room walls. The outflow grill 60 is in fluid communication with an exhaust duct 61 that discharges the exhaust air at a suitable location. The grill 60 permits an outflow of air from the room R that is equal to the inflow of fresh air from duct 35.

In using the apparatus of this invention, the damper 36 is adjusted so that the fresh air inflow is compatible with the number of people in the room and the heating or cooling load. The fresh air inflow results in air in the room exhausting through exhaust duct 61 whereby there is a reduction in objectionable odors in the room. The recycled air flow CFM is selected to provide a room air change rate that removes contaminants to meet the air quality cleanness desired. The recycled room air, for example 15 air filtered room air changes per hour, is controlled by the inflow grill members 42, 43, while the total air flow (discharged through the diffuser panel) is controlled by adjusting the blower speed. Accordingly, with the blower operating, air from the room interior is drawn through the grilled openings 41 into the plenum chamber 47 while air from duct 35 passes through the inlet 34 into said plenum chamber 47. Air in the plenum chamber 47 is drawn into the blower inlet 31 and discharged under pressure through duct 29 to the pressure plenum 24 whereupon it passes through the filter F and thence through the diffuser panel to flow downwardly generally as indicated by arrows 52. Assuming the unit 15 is generally in the central part of the room and there is only one such unit in the room, as the air flows downwardly it will diffuse and spread out as indicated by arrows 53, 54 toward the vertical room walls and thence upwardly and inwardly toward the grilled openings 41 such as indicated in FIG. 1.

With the apparatus of this invention, the air flow can be controlled so as to provide the desired amount of fresh make-up air flowing into the room with independent control of the recirculated air within the room, via room air change rate. Further, if necessary more than one of the modules 15 may be mounted in, for example, in the ceiling of a large room and connected to the source 50 in a manner previously indicated if one such module does not have the capacity to maintain an air quality of a desired cleanliness.

Even though the invention has been described with reference to the unit 15 being mounted in the ceiling, it is to be understood that it may be mounted in one of the vertical walls of the room to discharge toward the opposite vertical wall. For example wall 10 could be considered one side wall and wall 12 an opposite side wall while wall 20 of the housing would be a vertical rear wall rather than the top wall thereof.

What is claimed is:

1. Sterile air recycling apparatus mountable on a wall of a room for discharging air into the room interior comprising a housing having walls joined together to form a generally rectangular box shaped enclosure, the housing walls including a front wall, a rear wall, and opposite side walls, said front wall having an outlet opening, high efficiency filter means mounted within the housing in fluid communication with the front wall opening for discharging filtered air therethrough, a blower within the housing and having an inlet and an outlet, means for attaching the blower to the housing, means within the housing and connected to the blower outlet and to the filter means for placing the blower outlet in fluid communication with the filter means to supply air under pressure to the filter means to flow therethrough to the front wall outlet opening, the filter means including a HEPA filter, the blower, the filter means and the means for connecting the blower outlet to the filter means being connected to one another and mounted in housing to in conjunction with the housing define a space within the housing that comprises a negative pressure plenum chamber, the blower inlet opening to the negative pressure plenum to draw air therefrom, the opposite side walls each having a room air inlet opening to the negative pressure plenum chamber for having air drawn therethrough and into the negative pressure plenum chamber by the blower, the housing having a fresh air inlet opening to the negative pressure plenum chamber, and means connected to the housing for supplying fresh air from exterior of the room to the fresh air inlet, the means for placing the blower outlet in fluid communication with the filter means including wall means that in conjunction with the filter means defines a supply pressure plenum chamber in fluid communication with the filter means and having an inlet, and duct means connected between the blower outlet and the wall means for fluidly connecting the blower outlet to the supply pressure plenum chamber means inlet.

2. The apparatus of claim 1 further comprising means in the housing side wall inlets for controlling the volume of air flowing therethrough and wherein the means for supplying air to the fresh air inlet includes means for controlling the volume of air flowing to the fresh air inlet.

3. The apparatus as claimed in claim 1 wherein the housing includes opposite end walls, the fresh air inlet is in the rear wall, and there are provided mounting flanges joined to the housing side and end walls, the side walls air inlet openings being located more remote from the housing rear wall than the mounting flanges.

4. The apparatus of claim 3 wherein the housing includes a diffusion panel in the front wall outlet that has air passages therethrough for flow of air from the filter means to the room interior.

5. Sterile air recycling apparatus mountable on a wall of a room for discharging air into the room interior comprising a housing having walls joined together to form a generally rectangular box shaped enclosure, the housing walls including a front wall, a rear wall and opposite side walls, said front wall having an outlet opening, high efficiency filter means mounted in the housing and in fluid communication with the front wall opening for filtering air and discharging filtered air through the front wall opening, the filter means including a filter frame and HEPA filter material, plenum chamber walls within the housing that are joined together to in conjunction with the filter means define a pressure plenum chamber in fluid communication with the filter material, one of the plenum chamber walls having an inlet opening, a blower mounted within and to the housing and having an inlet opening within the housing exterior of the pressure plenum chamber and an outlet and means connecting the blower outlet to the inlet opening of the plenum chamber for placing the last mentioned inlet in fluid communication with the blower outlet, the opposite side walls each having a room air inlet opening into the housing exterior of the pressure plenum chamber and in air flow communication with the blower inlet for having air drawn therethrough by the blower, the housing having a fresh air inlet opening thereinto exterior of the pressure plenum chamber and remote from the side wall inlets.

6. The apparatus as claimed in claim 5 wherein the rear wall has the fresh air inlet and further comprising means connected to the rear wall for supplying fresh air and controlling the flow of fresh air to the rear wall inlet, mounting flanges joined to the side walls more remote from the rear wall than the side wall inlets, a diffuser panel mounted to the housing in the front wall outlet and having air passages therethrough to discharge air that passes through the filter means and a movable grill for each side wall inlet that is mounted to the respective side wall to control the volume of air flow through the respective side wall inlet.

7. The apparatus of claim 6 wherein the plenum chamber walls are spaced from each of the rear wall and the side walls.

* * * * *